US010076632B2

(12) United States Patent
Kim et al.

(10) Patent No.: US 10,076,632 B2
(45) Date of Patent: Sep. 18, 2018

(54) SENSORY FEEDBACK SYSTEM WITH ACTIVE LEARNING

(71) Applicant: International Business Machines Corporation, Armonk, NY (US)

(72) Inventors: Minkyong Kim, Scarsdale, NY (US); Min Li, San Jose, CA (US); Clifford A. Pickover, Yorktown Heights, NY (US); Valentina Salapura, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 283 days.

(21) Appl. No.: 14/850,999

(22) Filed: Sep. 11, 2015

(65) Prior Publication Data
US 2017/0072162 A1 Mar. 16, 2017

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2021/0027* (2013.01); *A61M 2021/0044* (2013.01); *A61M 2205/3368* (2013.01); *A61M 2205/3375* (2013.01)

(58) Field of Classification Search
CPC ......................................... A61M 21/00–21/02
See application file for complete search history.

(56) References Cited

U.S. PATENT DOCUMENTS

| 5,803,786 | A | 9/1998 | McCormick |
| 5,816,910 | A | 10/1998 | Steele et al. |
| 5,830,235 | A | 11/1998 | Standley |
| 6,592,425 | B2 | 7/2003 | Bapst et al. |
| 6,692,330 | B1 | 2/2004 | Kulick |
| RE39,791 | E | 8/2007 | Jurmain et al. |
| 2004/0177101 | A1 | 9/2004 | Underwood |
| 2015/0105608 | A1* | 4/2015 | Lipoma ............... A61B 5/6896 600/27 |
| 2015/0273698 | A1* | 10/2015 | Bender ................. B25J 11/009 701/23 |
| 2016/0292576 | A1* | 10/2016 | Pradeep ................... G06N 5/04 |
| 2016/0314673 | A1* | 10/2016 | Eyring ................... G08B 21/06 |

FOREIGN PATENT DOCUMENTS

CN 202724416 U 2/2013

OTHER PUBLICATIONS

Stacey, Kevin, "Cry analyzer seeks clues to babies' health", Brown University, Jul. 11, 2103, Printed on Jul. 17, 2015, 2 pages, <https://news.brown.edu/articles/2013/07/crybaby>.

(Continued)

*Primary Examiner* — Thaddeus Cox
(74) *Attorney, Agent, or Firm* — Isaac J. Gooshaw

(57) ABSTRACT

A computing device provides soothing output for a user. The computing device determines a type of soothing output that will soothe the user. The computing device provides the type of soothing output to the user. The computing device determines the level of distress of the user in response to the type of soothing output. The computing device modifies the first type of soothing output to a second type of soothing output if the level of distress meets or exceeds a threshold.

20 Claims, 5 Drawing Sheets

(56) References Cited

OTHER PUBLICATIONS

Weisul, Kimberly, "Looking for Growth Potential? Baby Products, Baby!", Inc., Published on: Mar. 25, 2014, Printed on Jul. 17, 2015, 3 pages, <http://www.inc.com/kimberly-weisul/looking-for-growth-potential-baby-products-baby.html>.

"Baby Care Products Market Will Reach USD 66.8 Billion Globally in 2017: Transparency Market Research", PR Newswire, Albany, New York, Apr. 2, 2012, Printed on: Sep. 10, 2015, 4 pages, <http://www.prnewswire.com/news-releases/baby-care-products-market-will-reach-usd-668-billion-globally-in-2017-transparency-market-research-145731275.html>.

* cited by examiner

SENSORY FEEDBACK SYSTEM WITH ACTIVE LEARNING

BACKGROUND OF THE INVENTION

The present invention relates generally to the field of providing feedback, and more particularly to adjusting feedback to reduce stress for a user.

The growth and development curves for young children are not only large but vary from one child to the next. The growth and development of any two children will not be the same. In addition, what is soothing for one child may not be soothing for another.

In most scenarios, there is a learning curve for caregivers. They must learn what soothes a particular child. They must also keep track of feeding times, cleaning times, nap times, etc. In some situations, such information is not readily available, such as with a daycare or a baby-sitter. This can make it more challenging to provide care for a child.

SUMMARY

Embodiments of the present invention provide a method, a computer system, and a computer program product to provide soothing output.

An embodiment of the present invention provides a method to provide soothing output. One or more processors detect an input that indicates at least one user needs to be soothed. The one or more processors determine a first type of soothing output that will soothe the at least one user. The one or more processors provide the first type of soothing output to the at least one user. The one or more processors determine the level of distress of the at least one user in response to the first type of soothing output. The one or more processors modify the first type of soothing output to a second type of soothing output if the level of distress meets or exceeds a threshold.

An embodiment of the present invention provides a computer program product to provide soothing output. One or more processors detect an input that indicates at least one user needs to be soothed. The one or more processors determine a first type of soothing output that will soothe the at least one user. The one or more processors provide the first type of soothing output to the at least one user. The one or more processors determine the level of distress of the at least one user in response to the first type of soothing output. The one or more processors modify the first type of soothing output to a second type of soothing output if the level of distress meets or exceeds a threshold.

An embodiment of the present invention provides a computer system to provide soothing output. One or more processors detect an input that indicates at least one user needs to be soothed. The one or more processors determine a first type of soothing output that will soothe the at least one user. The one or more processors provide the first type of soothing output to the at least one user. The one or more processors determine the level of distress of the at least one user in response to the first type of soothing output. The one or more processors modify the first type of soothing output to a second type of soothing output if the level of distress meets or exceeds a threshold.

DETAILED DESCRIPTION

Embodiments of the present invention recognize that each child is unique and that what soothes one child may not soothe another. Embodiments of the present invention recognize that monitoring of child interactions and reactions to various stimuli provides clues as to what a child may find soothing. Embodiments of the present invention recognize that a child caregiver would benefit from knowledge of what soothes a particular child or group of children. Embodiments of the present invention recognize that having more than one child to care for increases the difficulty of providing care for those children as care for each child must be tracked and maintained. Embodiments of the present invention recognize that it is not always possible to provide a desired soothing response for a child and that an alternative soothing stimuli may be beneficial in such circumstances. Some embodiments of the present invention recognize that soothing needs are not limited to children and, as such, provide soothing to adults and other living beings.

The present invention will now be described in detail with reference to the Figures.

Figure 1:
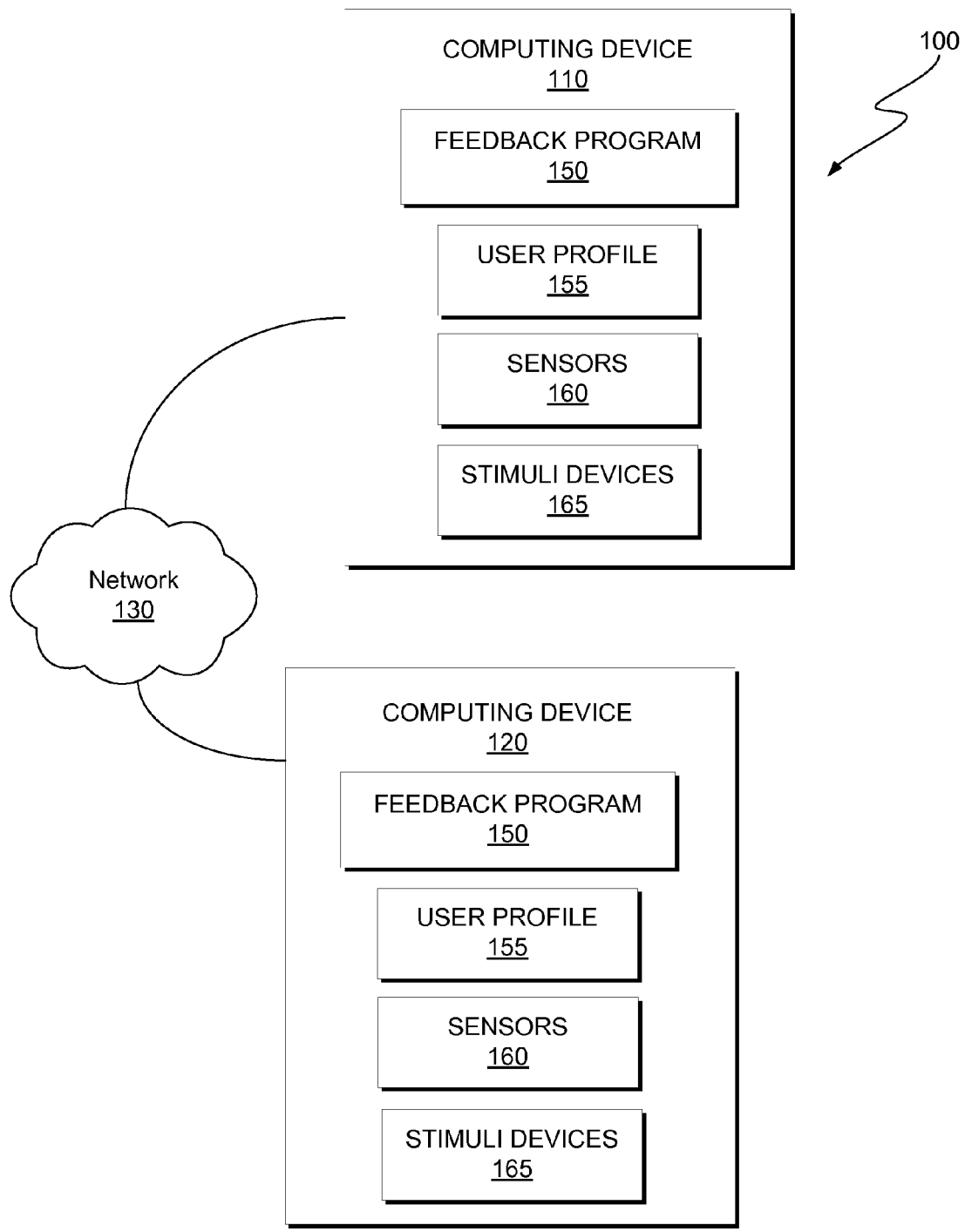
FIG. 1 is a functional block diagram illustrating a user feedback environment, in accordance with an exemplary embodiment of the present invention.

FIG. 1 is a functional block diagram illustrating a user feedback environment, generally designated 100, in accordance with one embodiment of the present invention. User feedback environment 100 includes computing device 110 and 120 connected over network 130. Computing device 110 and 120 each respectively include feedback program 150 and user profile 155. In the illustrated embodiment, computing device 110 and 120 each respectively include sensors 160 and stimuli devices 165. In general, stimuli devices 165 are specialized components that are configured to provide stimulation of a type to a user as directed by at least feedback program 150.

As used herein, the terms baby or child and their derivatives refer to any non-adult human or a user that is directly or indirectly interacting with feedback program 150 such that feedback program 150 provides feedback. However, it is to be noted that embodiments are not limited to soothing children. Some embodiments are configured to provide soothing to human beings of various age groups and levels of development. In some embodiments, other living creatures such as, for example, pets are monitored and soothed by feedback program 150. The concepts described below are readily understood by one skilled in the art and, as such, it is readily apparent how a pet, such as a cat or dog, could be monitored and soothed by an embodiment of feedback program 150.

In one embodiment, user profile 155 includes specific data regarding a particular baby. Such information includes, times of and scheduled times for care activities, such as feeding, bathing, sleep, and diaper changes etc. User profile 155 also includes detailed data regarding the response of the baby to particular types of stimuli. This includes associations between facial expression, audio and motion responses, etc., of a particular baby or group of babies, and a stimuli that has been determined to be soothing in that scenario. For example, user profile 155 includes data that indicates that a group of children are soothed by a light display accompanied by a particular audio stimulation.

In one embodiment, sensors 160 includes an ambient monitor that monitors forms of facial expression, audio and motion responses, etc., of a particular baby or a group of babies. In general, sensors 160 capture data needed by feedback program 150 to determine the source of and, in some cases, the level of stress being experienced by a baby. For example, the monitored information supplied to feedback program 150 via a microphone includes the sound from the baby and response from a parent (e.g. baby crying sound and patents' soothing response). In another example, the input includes one or more of a movement of the baby, a movement from a parent, a motion from a crib (e.g. rocking), etc. The input may also include the temperature near the baby, which in some embodiments, is used by feedback program 150 to determine whether the baby may be too cold or too hot, i.e., stressed. In one embodiment, sensors 160 also include a video camera that captures facial expressions of the baby, which are then interpreted by feedback program 150 when determining the mood of the baby.

In general, stimuli devices 165 include a variety of devices that can be used by feedback program 150 to provide soothing stimuli for the baby. In one embodiment, stimuli devices 165 include visual stimulation devices, such as for example, a colored-light emitting device. In some embodiments, this may be, for example, an array of light emitting diodes. In another embodiment, this is a display device such as a flat-screen display device. In one embodiment, stimuli devices 165 include audio devices, such as speakers. In one embodiment, stimuli devices 165 include tactile devices, such as, for example, devices that provide low intensity vibration to a baby. In one embodiment, stimuli devices 165 include a baby car-seat, bed, and mat that include massaging devices that, when activated, provide gentle massage stimulation to soothe the baby.

In various embodiments of the present invention, computing device 110 and 120 are each a computing device that can be a standalone device, a server, a laptop computer, a tablet computer, a netbook computer, a personal computer (PC), or a desktop computer. In another embodiment, computing device 110 and 120 represent a computing system utilizing clustered computers and components to act as a single pool of seamless resources. In general, computing device 110 and 120 can be any computing device or a combination of devices with access to sensors 160, feedback program 150 and user profile 155 and is capable of executing feedback program 150. In some embodiments, computing device 110 and 120 include internal and external hardware components, as depicted and described in further detail with respect to FIG. 3.

In this exemplary embodiment, feedback program 150 and user profile 155 are stored on computing device 110 and 120. However, in other embodiments, feedback program 150 and user profile 155 may be stored externally and accessed through a communication network, such as network 130. Network 130 can be, for example, a local area network (LAN), a wide area network (WAN) such as the Internet, or a combination of the two, and may include wired, wireless, fiber optic or any other connection known in the art. In general, network 130 can be any combination of connections and protocols that will support communications between computing device 110 and 120, and feedback program 150 and user profile 155, in accordance with a desired embodiment of the present invention.

In general, in one embodiment, feedback program 150 determines that i) at least one criteria has been met that indicates that soothing output from a first device is to be provided, and ii) that a first type of soothing output is to be provided based, at least in part, on a determination that the first type of soothing output will soothe at least one user. Then feedback program 150 uses the first device to provide the first type of soothing output to the at least one user. Feedback program 150 then modifies a selection criteria of the first type of soothing output based, at least in part, on a level of distress of at least one user that is determined after the first type of soothing output is provided. As user herein, distress refers to at least one of mental discomfort, physical discomfort or harmful situations experienced by a user. For example, emotion pain, physical pain, and an unhealthy increase in blood pressure are all types of discomfort.

In another embodiment, feedback program 150 detects an input that indicates at least one user needs to be soothed. Feedback program 150 determines a first type of soothing output that will soothe the at least one user. Feedback program 150 provides the first type of soothing output to the at least one user. Feedback program 150 determines the level of distress of the at least one user in response to the first type of soothing output. Feedback program 150 modifies the first type of soothing output to a second type of soothing output if the level of distress meets or exceeds a threshold.

In one embodiment, feedback program 150 determines that a given soothing output is to be provided based, at least in part, on a determination that the given soothing output will soothe both the at least one user and a second user.

In one embodiment, feedback program 150 determines that a second type of soothing output is to be provided based, at least in part, on one of i) a determination that the second type of soothing output will soothe the at least one user, and ii) a determination that the first type of soothing output has not reduced the level of distress of the at least one user to a threshold. Then feedback program 150 uses the first device to provide the second type of soothing output to the at least one user.

In one embodiment, feedback program 150 determines that a selection criteria of the second type of soothing output indicates that the second type of soothing output is to be provided.

In one embodiment, feedback program 150 determines a source of distress of the at least one user. Feedback program 150 then determines the first type of soothing output based, at least in part, on the source of distress of the at least one user.

In one embodiment, feedback program 150 predicts a future occurrence of distress for the at least one user based, at least in part, on a previous or current source of distress of the at least one user. Then feedback program 150 provides one or both of the first type of soothing output and the second type of soothing output before the at least one user experiences the source of distress.

In one embodiment, feedback program 150 determines one or both of the first type of soothing output and the second type of soothing output based, at least in part, on a matching between a characteristic of the at least one user and a characteristic included in a set of records that associate user characteristics with types of soothing output, wherein the characteristic includes at least one of i) vocalizations of the at least one user, ii) movement of the at least one user, iii) a history of behavior of the at least one user, iv) a stage of development of the at least one user, v) a schedule of care activity provided for the at least one user, and vi) an environment of the at least one user.

In one embodiment, feedback program 150 determines one or both of the first type of soothing output and the second type of soothing output based, at least in part, on a monitored soothing output that was previously provided to the at least one user by a caregiver.

In one embodiment, feedback program 150 indicates to a caregiver of the at least one user, a third type of soothing output to be provided to the at least one user.

In one embodiment, feedback program 150 analyzes an input, for example input data from a sensor, to determine that the at least one user is in distress. The input data is captured by a second device that monitors at least one of i) the at least one user, and ii) an environment of the at least one user.

In the following embodiment, feedback program 150 uses active learning and monitoring of a baby and its interactions with its world to create an automated soothing response to facilitate a degree of wellbeing, cognitive tone, and level of comfort for at least one of a baby and a person affected by an activity of the baby. In one example, the response produced by feedback program 150 includes a playback of sound from a parent, music, a motion of the crib, a photo or video of a parent or pet. In one example, the response produced by feedback program 150 includes controlling or otherwise adjusting the warmth of the crib, the motion of a mobile, a fun or educational video, or some other video or audio pattern typically used by the parents, which is a type of caregiver. Note that in certain embodiments, a caregiver is anyone that provides care for another being. For example, an employee of a retirement facility is a caregiver to the residents of that facility. In another example, the owner of a pet is the caregiver to that pet.

More particularly, one embodiment of feedback program 150 includes several components. The components include a multimodal ambient baby monitor for an initial baby input (e.g. feedback program 150 monitors baby/mom's interactive response). For instance, a baby may cry in a certain way, and a mother may respond vocally in an effective way to calm the baby. A correlation (learning) module learns what soothes baby. Thereafter, a new input from the baby is sensed, and based on said learning, a soothing output is created for baby. Other input and output options are described. The effectiveness of the soothing output (e.g., baby stopped crying) is used as one means of feedback to improve the effectiveness of feedback program 150 further.

At least one embodiment is configured for hands free use in a vehicle such that a level of stress experienced by one or more passengers, which may include a baby, is reduced. For example, a child does not enjoy car rides and begins making loud noises, which are both distracting and irritating for the driver and other passengers. As such, feedback program 150 determines the cause of the rising levels of stress for all of the passengers and determines a type of stimulation to provide the baby such that the baby ceases making the loud noise and the stress for all passengers is decreased accordingly.

As used herein, the term cognitive stimulus refers to stimulation of a child using one or more senses of the child including one of sound, touch, taste, smell, and visual feedback. In general such stimulus may be made available to the baby through, for example, a multimedia (video) output system that is part of a crib, a mobile, a toy, a car seat, a pacifier (for music playing or vibration), an electronic pet, a toy, etc. In one embodiment, the soothing output, i.e., the cognitive stimulus, is produced through a toy that may include a body portion having an interior cavity within which an audio device is disposed. In some embodiments, the body portion has a soft exterior surface. In one embodiment, the audio device has the capability of playing recorded sounds such as soothing music, user-recorded sounds such as a voice of a parent, or a combination of pre-recorded sounds and user-recorded sounds. In some embodiments, the toy is configured to cease operation after a predetermined period of time. In some embodiments, by setting the toy to a "voice-activated" mode, the toy can comfort a baby when necessary and turn itself off after the baby has fallen asleep.

In some embodiments, the cognitive stimulus is produced by a mobile for a baby's crib or playpen that includes a mobile. The mobile is mounted to the crib or playpen by means of a shaft that will move under the influence of vibrations from a motor, thereby imparting another type of motion to the mobile. In addition, an audio device, e.g., a sound chip, is incorporated into the device such that parents can play soothing music to the infant. In some embodiments, the recorder or sound chip is voice activated and has a mode switch which allows a parent to operate the mobile upon hearing noise, to turn the mobile on manually, or to turn the mobile off.

In some embodiments, the cognitive stimulus is produced by a blowing fan, i.e., a device included as part of stimuli devices 165 that also produces a soothing "humming" sound. In one such embodiment, a portable apparatus for soothing infants to enable them to fall asleep may utilize a portable housing having an intake and exhaust opening coupled by a hollow cylindrical tube into which is located a miniature motor disposed proximate to the intake opening with fan blades affixed on the rotating motor shaft that provides an air flow over a plurality of flexible members disposed proximate the exhaust opening. A control arrangement, coupled to a battery power source, is disposed within the housing for controlling the amount of forced air flowing out of the exhaust opening so that the tone or the sounds emanating from the apparatus can be controlled.

In some embodiments, the cognitive stimulus may make use of a pacifier connected to a pressure transducer. The pressure transducer serves to detect sucking intensity and time of sucking. The pacifier/feedback program 150 system activates a sound source, such as a music source, upon sucking of a minimum intensity being detected for a minimum period of time.

In general, feedback program 150 provides such stimulation in such a manner that a determined level of stress for the child is decreased. Such stresses may take a variety of forms including for example, a sense of boredom, vulnerability or loneliness as experienced by the baby. For example, the feedback provided to a baby by feedback program 150 increases the sensation of well-being experienced by the baby, while decreasing the level of boredom experienced by the baby. In one embodiment, feedback program 150 uses data from sensors 160 to determine a stress level for a particular type of stress and then provides a cognitive stimulus that is predicted to decrease that type of stress.

In exemplary embodiments, feedback program 150 learns what soothes a baby, and that this may be different in different contexts (e.g. in a car, in a crib, time of day, etc.).

In some embodiments, feedback program 150 learns what sooths the cohorts, e.g., friends, acquaintances, of a particular baby. Such embodiments recognize that babies with certain kinds of characteristics, such as for example, dispositions, ages, cognitive characteristics, and disorders may respond differently, and it is interesting and useful to keep track of this not only for one baby but for a "cohort." In this manner, babies other than a particular baby may benefit from a cloud-based assessment module and database for such cohorts.

In some embodiments, feedback program 150 is employed as a coach for less experienced parents. Additionally, parents may teach the unit explicitly about helpful measures that soothe a baby, and this can be of use to alternate caregivers of that baby.

In some embodiments, feedback program 150 the learned soothing stimulus produced by feedback program 150 is changed through time, thus changing the output in an adaptive manner. For example, the output might select the current favorite song, videos, or other responses, which are currently most successful. In one such embodiment, feedback program 150 is configured to adapt its learning approach as the development of the child progresses, which is a characteristic of the child. As such, the selection criteria for a type of soothing to be provided changes as the child changes. In one such embodiment, feedback program 150 adapts to predicted changes in behavioral patterns as the baby grows and develops. In one such embodiment, as the baby grows to one year old, the baby (or toddler) might not like a consistent rushing (white or pink) noise any more, but prefers instead some other audio/video response that requires a higher level of cognitive attention to identify and appreciate, for example, bird song.

In some embodiments, feedback program 150 tracks infant cries and a history of cries for a given baby over a period of time, which may be set by the caregiver. In some embodiments, feedback program 150 tracks, for example, behavioral patterns of a baby that are associated with a distressed period, and multiple behavior modes, e.g., differences in the frequency of the demand events and/or the duration of the demand events.

In some embodiments, feedback program 150 employ a crying analyzer module that analyzes the cries of babies, searching for clues to potential problems. Slight variations in cries, mostly imperceptible to the human ear, can be a "window into the brain" that could allow for early intervention. In some embodiments, feedback program 150 may operates in two phases. During the first phase, feedback program 150 separates recorded cries into regular portions and then analyzes those portions using a number of parameters. During a second phase, feedback program 150 uses data from the first phase to generate a broader view of the cry and reduces the number of parameters to those that are determined to be most useful in making determinations regarding stress levels of the baby.

For example, in one embodiment, a crying analyzer module of feedback program 150 separates recorded cries into 12.5-millisecond frames. Each frame is analyzed for several parameters, including frequency characteristics, voicing, and acoustic volume. The frames are put back together and characterized either as an utterance, for example a single "wah", as silence, or as a pause between utterances. In some scenarios and embodiments, longer utterances are separated from shorter ones and the time between utterances is recorded. Pitch, including the contour of pitch over time, and other variables can then be averaged across each utterance. Together with various information such as eating schedules, the temperature around a baby, and other monitored information of a baby, feedback program 150 estimates one or more possible variables that possibly suggest why the baby is crying.

In some scenarios and embodiments, feedback program 150 may be unable to discern a reason for the stress being experienced by a baby, but, nonetheless, feedback program 150 may be configured to attempt to sooth the baby even if no guidance is determined due to the lack of an identified source of stress. For example, in one scenarios and embodiment, a baby has an upset stomach, feedback program 150 does not have access to any data that indicates that this is the source of the stress being experienced by the baby. As such, feedback program 150 executes a series of trial and error attempts to identify a cognitive stimulus that will reduce the level of stress of the baby, i.e., feedback program 150 varies the cognitive stimulus being provided to the baby until there is a determined result indicating that the level of stress of the baby is decreased. In some embodiments, feedback program 150 uses such scenarios as a basis to handle similar situations that occur. For example, the baby was soothed by colored light that slowly changed hues. As such, if a similar scenario occurs in the future, feedback program 150 will begins its trial and error attempts using the colored light that slowly changed hues. Similarly, feedback program 150 may track infant cries and eating history for possible correlations and to aid in the learning process. In some embodiments, this type of scenario and learned "lessons" may be augmented using other data, such as for example, a time of day. In some embodiments, such data helps feedback program 150 to learn correlations between infant unhappiness, cognitive state, and temporal factors.

In some embodiments, feedback program 150 considers the context in which the baby is in. In one embodiment and scenario, feedback program 150 determines that, based on context, one soothing mechanism is more appropriate than others for context. For example, if the baby is in a car-seat for babies, then feedback program 150 determines that, based on the context, that only cognitive stimulus should be provided that minimizes the level of distraction to the driver. Another example would be, whether it is time to feed the baby. For example, if feedback program 150 determines, based on the last recorded feeding time, that the baby is crying because they are hungry, then feedback program 150 provides a soothing voice suggesting to the baby to wait a bit since such a response would be more appropriate than, for example, playing a lullaby. Of course, depending on age, the baby may not understand the complexity of such messages, but the tone of such messages may still serve to sooth and reassure the baby that their needs will shortly be met.

In some embodiments, feedback program 150 may employ active learning, a special case of semi-supervised machine learning in which a learning algorithm is able to interactively query the user (or some other information source) to obtain the desired outputs. In some embodiments, such other data may be stored in the cloud or social network to aid a machine learning unit of feedback program 150. Such data may include, for example, feeding data, diaper data, sleeping data, data indicating predicted temperament of the baby, temperature data, medicine data, and water or other non-milk fluid data, milk data, emergency contact data, allergy data, and schedule or appointment data. Certain comforting toys might also be indicated, which may be indicated to a caregiver that is not fully familiar with the baby. For example, it is time for bed for a baby, a babysitter is new to a household and the baby is crying without an apparent cause, feedback program 150 identifies that the baby has a favorite stuffed toy that they sleep with and advises the babysitter to make that toy available to the child.

In some embodiments, feedback program 150 monitors the effectiveness of the soothing output together with the baby crying analysis (e.g., replay of mother's facial expression with sounds) and uses it as the feedback to enhance the correlation/learning component of feedback program 150.

This has a personalization effect, as different babies may prefer different soothing mechanisms. In some scenarios and embodiments, feedback program 150 monitors the soothing response from a parent or caregiver and learns which soothing responses are more effective. For example, feedback program 150 monitors three instances of similar crying and body language of the child and also notes three different responses that were used by a caregiver. Feedback program 150 then determines which response from the caregiver was most effective at soothing the child under those circumstances and uses it to provide soothing to the child during future circumstances that correlate to the three instances that were monitored. Feedback program 150 then uses this knowledge when determining which soothing response to correlate with a given circumstance. In other words, feedback program 150 monitors the activity of a caregiver to discover which soothing response is most effective and uses that knowledge to improve its ability to provide a soothing response for the child.

Figure 2:
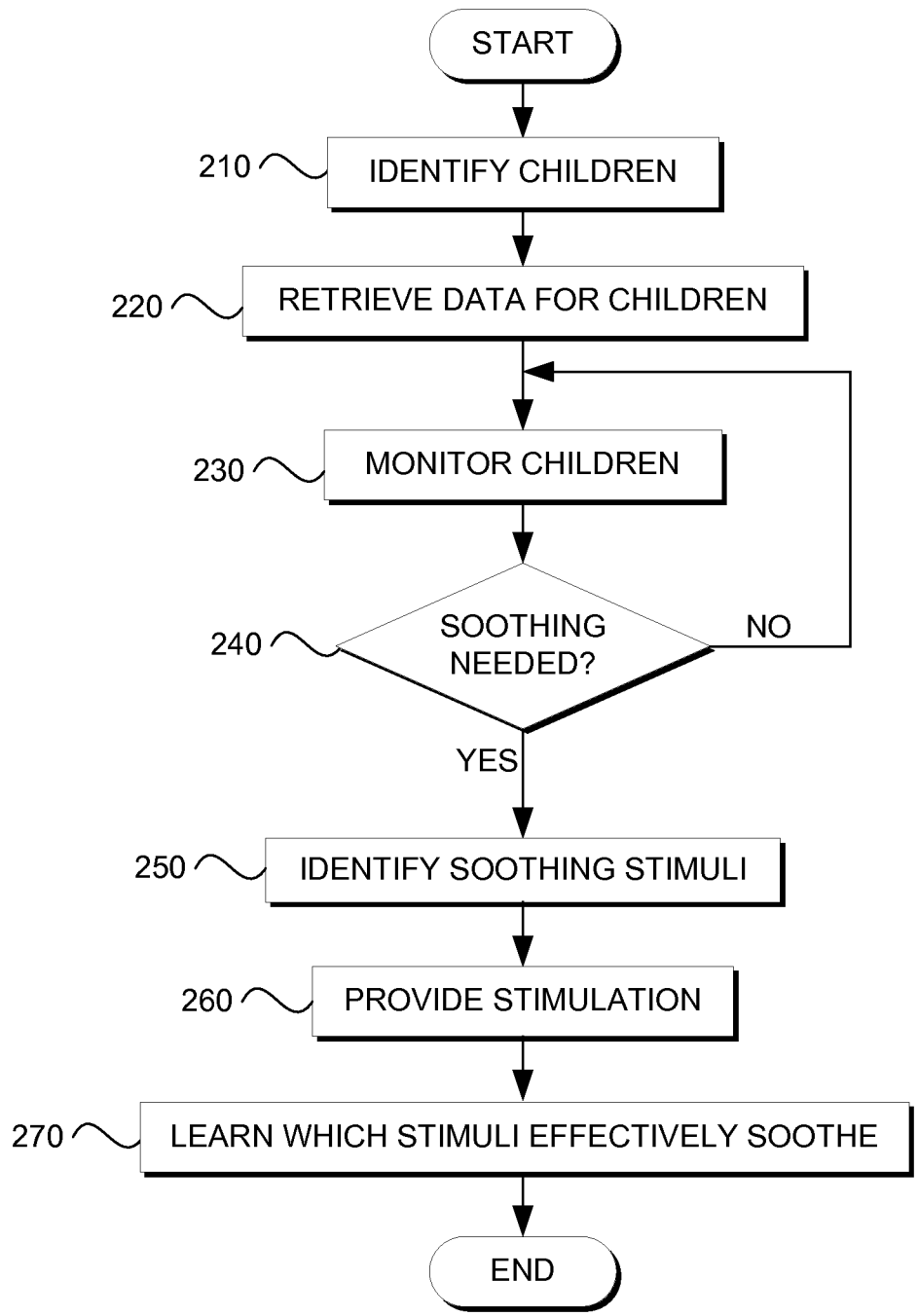
FIG. 2 illustrates operational processes of a feedback program, executing on a computing device within the environment of FIG. 1, in accordance with an exemplary embodiment of the present invention.

FIG. 2 illustrates operational processes of a feedback program, executing on a computing device within the environment of FIG. 1, in accordance with an exemplary embodiment of the present invention.

In process 210, feedback program 150 uses data from sensors 160 and user profile 155 to identify the children to be monitored and soothed. In some scenarios, this is a single child, in other scenarios this is a group of children. For example, feedback program 150 uses audio data from sensors 160 to identify the parents of child A. In this scenario and embodiment, the voice patterns of the parents are included as part of user profile 155 and feedback program 150 applies a simple matching process to identify the parents of the child. Therefore, feedback program 150 determines that there is a high probability that child A is present and uses other data from sensors 160 to confirm the presence of the child. In this example, video data is captured by a camera and feedback program 150 analyses this data using facial recognition. Both the parents and the child are identified using stored facial data included in user profile 155. In another example, feedback program 150 receives direct confirmation from the parents, via user data entry, indicating that child A is present.

In process 220, feedback program 150 retrieves data regarding each identified child from user profile 155. In some scenarios and embodiments, a child was identified in process 210 that was not included in the local copy of user profile 155. In such a case, feedback program 150 may prompt the parents or care provider to provide an identity for the unknown child, hereafter called child B. In some embodiments and scenarios, feedback program 150 accesses a database that includes user profile 155 that corresponds to child B. In general, feedback program 150 accesses data that indicates known behavioral patterns of the children and stimuli that are known to soothe the children. For example, child A is known to become irritable an hour before naptime, user profile 155 for child A includes an association between such a behavior pattern and a light display that has been shown to soothe child A when child A displays that behavioral pattern.

In process 230, feedback program 150 begins monitoring child A for behavioral patterns that indicate that child A is in distress. For example, feedback program 150 monitors i) the facial expression of child A, ii) the line of sight of child A, iii) audible response of child A, and iv) the body language of child A. Additionally, feedback program 150 also monitors the environment of child A. In this embodiment, feedback program 150 also monitors the surroundings of child A to identify potential sources of distress. This may include both nearby environmental elements, such as the temperature of the baby, as well as more distant elements such as the changing surroundings that are viewable from inside a moving vehicle.

In decision process 240, feedback program 150 determines, based on an analysis of data gathered in process 230, whether soothing is needed by the child. In general, if a criteria has been met that indicates that soothing output from a first device is to be provided, then feedback program 150 determines that feedback is to be provided. For example, based on such an analysis of child A, feedback program 150 determines that child A has a facial expression that is associated with fear. In addition, child A is showing body language of clenched hands and both their arms and legs are retracted towards the core of their body. Feedback program 150 determines that this body language matches a pattern of body language that corresponds to fear. As such, feedback program 150 determines that soothing is needed, (determination process 240, YES branch), and proceeds to process 250. If feedback program 150 determines that soothing is not needed, (determination process 240, NO branch), then feedback program 150 proceeds to process 230.

In process 250, feedback program 150 identifies a soothing response based on the behavioral pattern being displayed by child A. In general, feedback program 150 identifies a type of soothing output to be provided based, at least in part, on a determination that the type of soothing output will soothe the user that is in distress. Continuing with the above example, feedback program 150 determines that a change in the behavioral pattern of child A coincided with a change in the line of sight of child A. Feedback program 150 reviews video imaging that includes the object that drew the attention of child A. In this example, a statue of a large animal drew the attention of child A. Feedback program 150 identifies that there is an animal included in the video imaging that likely frightened child A. In response, feedback program 150 determines that gentle, re-assuring stimuli should be provided to reduce the distress of child A. As such, in process 260, feedback program 150 uses stimuli including a video of a sunrise combined with a recorded audio segment of the mother of child A that feedback program 150 previously captured during a previous excursion that included passing the statue of the large animal.

In process 270, feedback program 150 learns which stimuli effectively soothe the user. In general, feedback program 150 modifies its selection process for determining soothing stimuli based on the effectiveness of the type soothing provided in process 260. In general, feedback program 150 modifies a selection criteria regarding the type of soothing output to be provided, when presented with results that match, to within a threshold, the results of the analysis of data gathered in process 230. Such a modification is based, at least in part, on a level of distress of the user after the first type of soothing output is provided. In some cases, the level of distress is determined after a period of time such that the effectiveness of the soothing is more readily apparent. In one example, a set of potential soothing stimuli are associated with a given set of circumstances, which includes user characteristics. In this example, the set of potential soothing stimuli are ordered, based on a weighted average for each potential soothing stimuli, such that it takes into account the number of times a user was successfully soothed by a particular stimuli. In one such embodiment, failure of a given stimuli to soothe a user to within a threshold reduces the weighted value for that stimuli. As such, the selection process is modified such that, when feedback program 150 makes future selections of stimuli based on the greatest weighed value, the failure of that given stimuli to reduce the distress of the user is accounted for.

In general, feedback program 150 is configured to i) analyze the data gathered by sensors 160, and ii) determine a causal relationship between an element identified in that analysis and a resulting distress of the child. In one example, feedback program 150 receives motion data from accelerometers included as part of sensors 160. The analysis indicates a sudden rise and fall in the elevation of the child followed by a harmonic and decreasing rise and fall pattern of motion. In addition, feedback program 150 receives motion data from GPS sensors included as part of sensors 160. Analysis of this GPS motion data indicates that the child is in a moving vehicle. As such, feedback program 150 determines that the likely source of distress of the child was due to hitting a bump by the vehicle and responds accordingly. In a similar example, there is no harmonic and decreasing rise and fall pattern of motion. However, there is another child within close proximity to the first child. Analysis of video footage provided by sensors 160 indicates that this other child was touching the car seat of the distressed child. As such, feedback program 150 determines that the likely source of distress of the child was due to being jostled by the other child and responds accordingly. In this example, feedback program 150 issues a message to the other child with instructions to be more cautious with their movements and informs the caregiver of the situation. In yet another example, i) the analysis of video footage provided by sensors 160 indicates that this other child was touching the face of the distressed child, and ii) analysis of the accelerometer data and GPS motion data indicate that the vehicle is moving smoothly, i.e., no bump was encountered. As such, feedback program 150 determines that the likely source of distress of the child was due to being touched by the other child and responds accordingly.

In one embodiment, feedback program 150 has a set of stimuli available with which to soothe a distressed child. In one such embodiment, this set corresponds to a number of visual, audio and touch based stimuli. In some scenarios and embodiments, feedback program 150 selects one or more of these stimuli and applies it to soothe a child that has displayed a certain behavioral pattern. If the child is soothed then feedback program 150 makes note of that success and uses this knowledge for future instances of that behavioral pattern.

In some embodiments, feedback program 150 uses a series of different stimuli and notes the effectiveness of each at soothing the child. In general, feedback program 150 learns which stimuli are effective at soothing the child by testing them on the child, and uses this knowledge when selecting soothing stimuli for that child when the child displays a certain behavioral pattern. In some embodiments, various combinations of stimuli are tested by feedback program 150 when determining which stimuli are effective at soothing a child that has displayed a certain behavioral pattern. In some embodiments, a set of likely soothing stimuli responses are initially indicated by a caregiver, e.g., a parent, which may decrease the amount of learning required by feedback program 150 when determining what stimuli will soothe the child.

In some scenarios and embodiments, feedback program 150 determines, at least in part, which stimuli to use based on both the distressed child but also on the presence of other children. In some such embodiments, a stimuli is selected that is i) likely to soothe the distressed child, and ii) is less likely to cause distress for the other children present. Some such embodiments access the user profile of each child and use the data therein when making this statistical determination. One of ordinary skill in the art will appreciate that any type of statistical analysis may be used without deviating from the invention. As such, discussion of a specific type of analysis is unnecessary for the purposes of this disclosure.

In some embodiments, feedback program 150 updates user profile 155 with specific data to be used when certain scenarios arise. For example, in continuation with the above example, based on the repeated occurrence of distress of child A when child A views the statue of the large animal, feedback program 150 updates user profile 155 with instructions such that feedback program 150 provides distracting stimuli the next time the vehicle is approaching the statue of the large animal. In this scenario and embodiment, feedback program 150 has access to global positioning system (GPS) data that indicate the location of the statue of the large animal. In some embodiments, feedback program 150 is configured to gather such data using sensors 160, which in this embodiment include a GPS locator. As such, feedback program 150 is able to determine the general location of the statue of the large animal. Further, in this scenario and embodiment, feedback program 150 also determines the location, velocity and direction of movement of the vehicle. As such, feedback program 150 determines a likely time in which the statue will become viewable by child A and begins to provide distracting stimulation before child A can see the statue. As such, during this excursion, child A does not see the statue and feedback program 150 determines that distress of the child has been reduced. As such, in some scenarios and embodiments, the distress of a child is predicted to occur and feedback program 150 takes action, e.g., provides stimulation, to prevent the realization of that predicted distress. In some embodiments, feedback program 150 notifies the caregiver of the most likely cause for an occurrence of distress. This allows the caregiver to take action to assist in preventing future occurrences of such distress.

In this embodiment, feedback program 150 employs active learning to identify stimuli to soothe a baby when the baby is distressed. In some embodiments, feedback program 150 actively monitors behavioral patterns of both the baby and its caregivers. Feedback program 150 analyzes and uses this data to identify relationships between certain events and stimuli that soothed the baby. For example, feedback program 150 identifies that the baby is distressed based on facial expression and crying. Feedback program 150 also determines that this behavioral pattern does not match any known behavioral patterns included in user profile 155. Feedback program 150 notifies the caregiver that the baby is in distress. Feedback program 150 then monitors the response of the caregiver and the results of that response. For example, the caregiver determines that the child is hungry, but since the child and caregiver are in a moving vehicle, the caregiver audibly re-assures the child and indicates that they will be home soon and that the child can have something to eat then. Feedback program 150 records the verbal response of the caregiver and saves it as part of user profile 155. Then during a future recurrence of the behavioral pattern of the child when traveling in a vehicle, feedback program 150 replays the recorded response to soothe the child. Feedback program 150 also notified the parent that the child is likely hungry.

In some embodiments, the successful soothing of a child is noted by feedback program 150 and is used to re-affirm that a proper response to a particular behavioral pattern has been identified. In one embodiment, feedback program 150 uses statistical analysis to identify a list of responses that are most likely to soothe the child. As various responses are tried by feedback program 150, the most successful ones are move up the list such that, in the future, they are tried before the less successful ones.

In some embodiments and scenarios, if an unknown behavioral pattern is identified, feedback program 150 accesses a database of reference behavioral patterns, not shown in FIG. 1 but is accessible via network 130, and identifies the closest match to the behavioral pattern being displayed by the child. Feedback program 150 then retrieves a set of responses, i.e., stimuli, that are associated with that reference behavioral pattern. These responses are then used by feedback program 150 in an attempt to soothe the child. In some such embodiments, feedback program 150 returns the results of this attempt and the set of responses that are associated with the reference behavioral pattern are updated based on the success of soothing the child. In some scenarios, such an approach can reduce the amount of trial and error needed to identify a stimuli that will soothe a child. In some scenarios and embodiments, feedback program 150 uses such a database to identify a stimuli that will likely soothe a group of children based on a statistical likelihood of success. As such, not only is the child displaying a particular behavioral pattern soothed but the other children in the group are also soothed before they can display a similar behavioral pattern. As such, in some embodiments, multiple computing devices hosting instances of feedback program 150 contribute to and update the database of reference behavioral patterns. Therefore, in such embodiments, a given instance of feedback program 150 has access to a large corpus of reference behavioral patterns that have associated stimuli that are predicted to soothe a given child for a given set of circumstances. Such circumstances can include both factors that are locally specific to the child and scenario itself but also other factors, such as time of year. In general, feedback program 150 identifies correlations between child behavioral patterns and stimuli/responses that reduce incidence/duration of those behavioral patterns. Feedback program 150 then uses those correlations to update the database of reference behavioral patterns.

In some embodiments, some or all of the functions of feedback program 150 are performed on an external computing system that is in contact with one or both of components of computing device 110 and 120. Such an embodiment may therefore have increased access to computing resources needed to perform the analytical processes of feedback program 150 as described herein. Such analytical processes include, for example, statistical analysis, identification of distress of a child, determination of a stimuli that is likely to soothe the child, and analysis of data provided by sensors 160.

In one embodiment configured for use by adult human beings, feedback program 150 determines a level of stress/distress for a particular person. Based on this determination, feedback program 150 determines whether a type of soothing is to be provided. In some such embodiments, environmental limits are taken into account when determining a type of soothing to be provided. For example, an employee in an office that is shared with a fellow employee is wearing a smart device that includes sensors to monitor the heart rate and blood pressure of that employee. In this example, the smart device is included as part of sensors 160. Based on this data, feedback program 150 determines that there has been a substantial increase in the level of stress of that employee. Therefore, feedback program 150 determines that a soothing response is to be provided. In this example embodiment, feedback program 150 takes into account limitations associated with the work environment. For example, certain types of music or decibel levels are deemed inappropriate by the workplace. As such, feedback program 150 treats the workplace as though it were another user with their own preferences and takes those preferences into account when selecting a type of soothing to be provided. As such, the workplace, and the fellow employee, have their own user profile 155 that feedback program 150 accesses when making a determination as to which type of soothing to provide to the employee. In this example, feedback program 150 determines that soft music without lyrics is appropriate along with the activation of a massage function of the chair that the employee is occupying. In this example, both the chair and a device that plays the music are included as part of stimuli devices 165. Based on a change in the level of stress of the employee after the soothing stimuli is applied, feedback program 150 modifies its selection process such that effective soothing stimuli is provided in the future.

Figure 3:
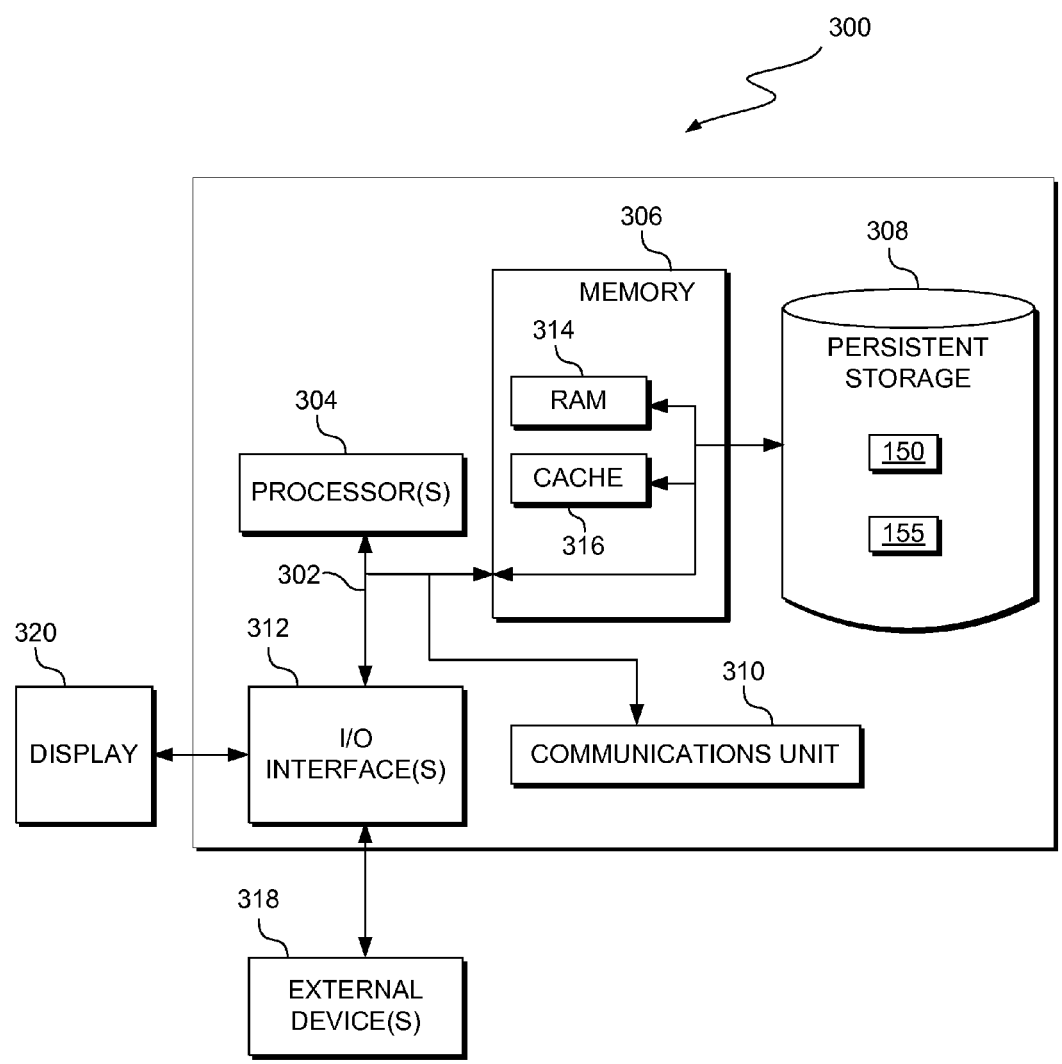
FIG. 3 depicts a block diagram of components of the computing device executing the feedback program, in accordance with an exemplary embodiment of the present invention.

FIG. 3 depicts a block diagram, 300, of components of computing device 110 and 120, in accordance with an illustrative embodiment of the present invention. It should be appreciated that FIG. 3 provides only an illustration of one implementation and does not imply any limitations with regard to the environments in which different embodiments may be implemented. Many modifications to the depicted environment may be made.

Computing device 110 and 120 each include communications fabric 302, which provides communications between computer processor(s) 304, memory 306, persistent storage 308, communications unit 310, and input/output (I/O) interface(s) 312. Communications fabric 302 can be implemented with any architecture designed for passing data and/or control information between processors (such as microprocessors, communications and network processors, etc.), system memory, peripheral devices, and any other hardware components within a system. For example, communications fabric 302 can be implemented with one or more buses.

Memory 306 and persistent storage 308 are computer-readable storage media. In this embodiment, memory 306 includes random access memory (RAM) 314 and cache memory 316. In general, memory 306 can include any suitable volatile or non-volatile computer-readable storage media.

Feedback program 150 and user profile 155 are stored in persistent storage 308 for execution and/or access by one or more of the respective computer processors 304 via one or more memories of memory 306. In this embodiment, persistent storage 308 includes a magnetic hard disk drive. Alternatively, or in addition to a magnetic hard disk drive, persistent storage 308 can include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 308 may also be removable. For example, a removable hard drive may be used for persistent storage 308. Other examples include optical and magnetic disks, thumb drives, and smart cards that are inserted into a drive for transfer onto another computer-readable storage medium that is also part of persistent storage 308.

Communications unit 310, in these examples, provides for communications with other data processing systems or devices, including resources of network 130. In these examples, communications unit 310 includes one or more network interface cards. Communications unit 310 may provide communications through the use of either or both physical and wireless communications links. Feedback program 150 and user profile 155 may be downloaded to persistent storage 308 through communications unit 310.

I/O interface(s) 312 allows for input and output of data with other devices that may be connected to computing device 110 and 120. For example, I/O interface 312 may provide a connection to external devices 318 such as a keyboard, keypad, a touch screen, and/or some other suitable input device. External devices 318 can also include portable computer-readable storage media such as, for example, thumb drives, portable optical or magnetic disks, and memory cards. Software and data used to practice embodiments of the present invention, e.g., feedback program 150 and user profile 155, can be stored on such portable computer-readable storage media and can be loaded onto persistent storage 308 via I/O interface(s) 312. I/O interface(s) 312 also connect to a display 320.

Display 320 provides a mechanism to display data to a user and may be, for example, a computer monitor, or a television screen.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
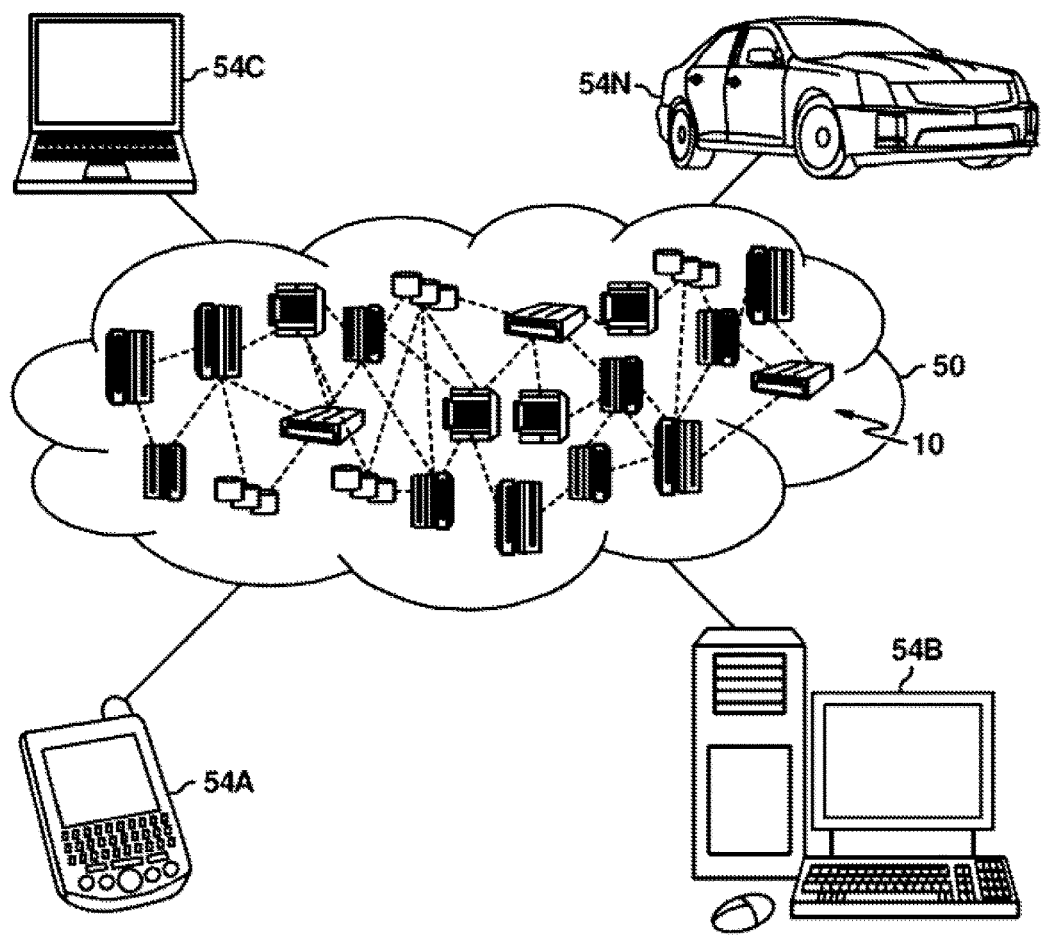
FIG. 4 depicts a cloud computing environment according to an embodiment of the present invention.

Referring now to FIG. 4, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
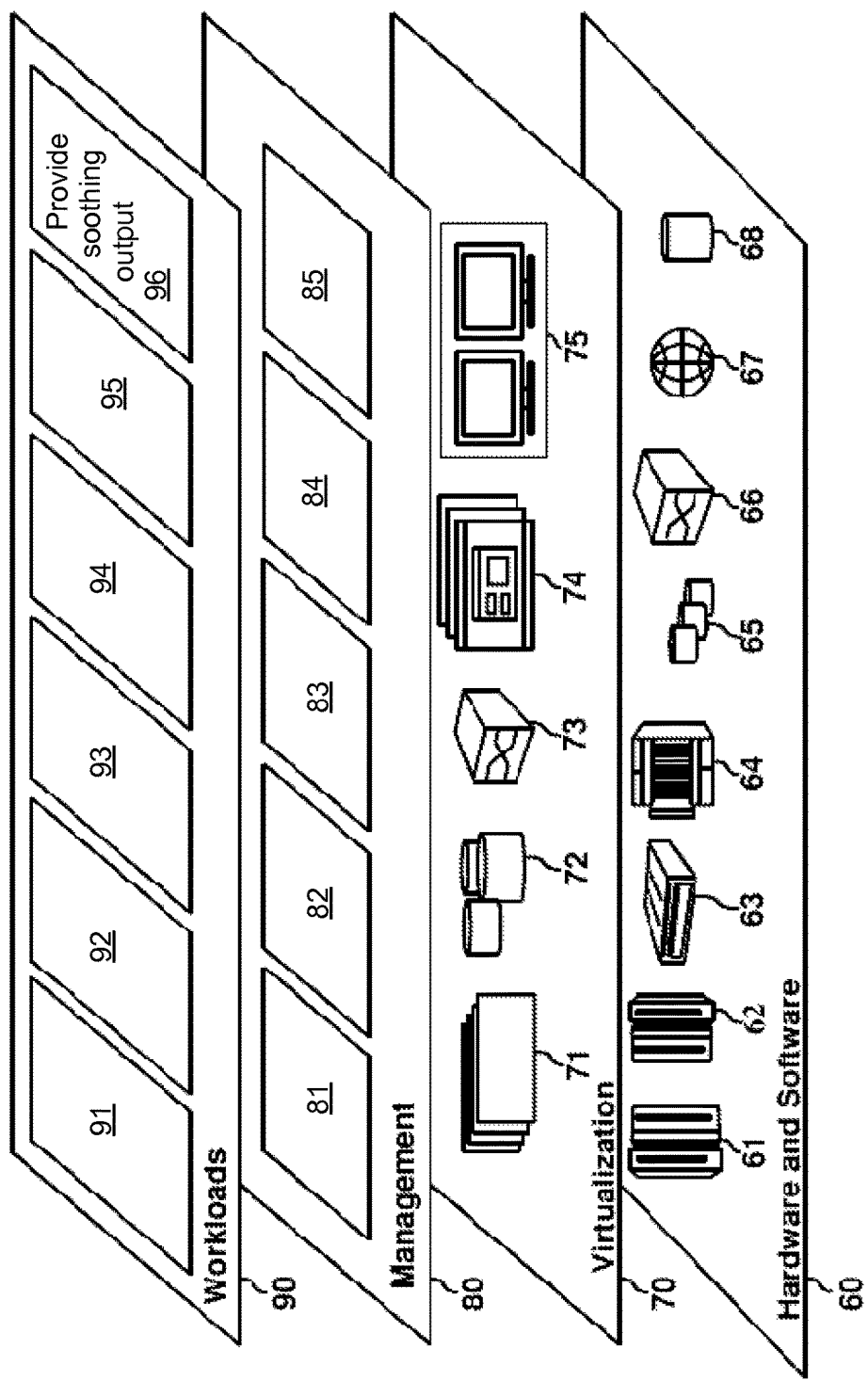
FIG. 5 depicts abstraction model layers according to an embodiment of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and providing soothing output 96.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

It is to be noted that the term(s) "Smalltalk" and the like may be subject to trademark rights in various jurisdictions throughout the world and are used here only in reference to the products or services properly denominated by the marks to the extent that such trademark rights may exist.

What is claimed is:

1. A method of computer learning to provide soothing output via a soothing device, the method comprising:
monitoring, by one or more processors, input from a plurality of sensors, wherein the sensors are configured to measure one or both of (i) environmental conditions surrounding one or more users and (ii) a state of the one or more users;
detecting, by the one or more processors, a sensor input from the plurality of sensors that meets at least one criteria that indicates that soothing output from a first device is to be provided to at least one user;
generating, by the one or more processors, a determination that a first instance of soothing output is to be provided based, at least in part, on a determination that a first type of soothing output is predicted to soothe at least one user based, at least in part, on a set of selection criteria that are stored in computer memory;
generating, by the one or more processors, the first instance of soothing output by sending a first set of electronic signals that activate the first device, wherein, post activation, the soothing output generated by the first device (i) includes the first type of soothing output and (ii) is configured to be detectable by one or more senses of the at least one user;
generating, by the one or more processors, at least one modified selection criteria based on a given selection criteria of the set of selection criteria, wherein the given selection criteria (i) is stored in computer memory and (ii) is modified based, at least in part, on a determined level of distress of the at least one user that is determined after the first type of soothing output is generated for a time period;
determining that a second type of soothing output is predicted to increase a level of soothing of the at least one user based, at least in part, on the at least one modified selection criteria; and
responsive to the level of distress of the at least one user at least meeting a threshold after the first type of soothing output is generated for the time period, generating, by the one or more processors, a second instance of soothing output, for the at least one user, by sending a second set of electronic signals that activate the first device, wherein the second instance of soothing output includes soothing output that is selected based on both the first type of soothing output and the second type of soothing output.

2. The method of claim 1, the method including:
determining, by the one or more processors, that a given soothing output is to be provided based, at least in part, on a determination that the given soothing output will soothe both the at least one user and a second user.

3. The method of claim 1, the method including:
determining, by the one or more processors, that the second type of soothing output is to be provided based, at least in part, on a determination that the second type of soothing output will soothe the at least one user; and
using, by the one or more processors, first device to provide the second type of soothing output to the at least one user.

4. The method of claim 3, the method including:
determining, by the one or more processors, that a selection criteria of the second type of soothing output indicates that the second type of soothing output is to be provided.

5. The method of claim 1, the method including:
determining, by the one or more processors, a source of distress of the at least one user; and
determining, by the one or more processors, the first type of soothing output based, at least in part, on the source of distress of the at least one user.

6. The method of claim 5, the method including:
predicting, by the one or more processors, a future occurrence of distress for the at least one user based, at least in part, on a known source of distress for the at least one user; and
providing, by the one or more processors, the first type of soothing output before a subsequent exposure of the at least one user to the known source of distress.

7. The method of claim 1, the method including:
determining, by the one or more processors, one or both of the first type of soothing output and the second type of soothing output based, at least in part, on a matching between a characteristic of the at least one user and a characteristic included in a set of records that associates user characteristics with types of soothing output, wherein the characteristic includes at least one of i) vocalizations of the at least one user, ii) movement of the at least one user, iii) a history of behavior of the at least one user, iv) a stage of development of the at least one user, v) a schedule of care activity provided for the at least one user, and vi) an environment of the at least one user.

8. The method of claim 1, the method including:
determining, by the one or more processors, one or both of the first type of soothing output and the second type of soothing output, at least in part, on a monitored soothing output that was previously provided to the at least one user by a caregiver.

9. The method of claim 1, the method including:
indicating, by the one or more processors, to a caregiver of the at least one user, a third type of soothing output to be provided to the at least one user.

10. The method of claim 1, the method including:
analyzing, by the one or more processors, the input to determine that the at least one user is in distress, wherein the input is captured by a second device that monitors at least one of i) the at least one user, and ii) an environment of the at least one user.

11. A computer program product for computer learning to provide soothing output, the computer program product comprising:
one or more computer-readable storage media and program instructions stored on the one or more computer-readable storage media, the program instructions comprising:
program instructions to monitor input from a plurality of sensors, wherein the sensors are configured to measure one or both of (i) environmental conditions surrounding one or more users and (ii) a state of the one or more users;
program instructions to detect a sensor input from the plurality of sensors that meets at least one criteria that indicates that soothing output from a first device is to be provided to at least one user;
program instructions to generate a determination that a first instance of soothing output is to be provided based, at least in part, on a determination that a first type of soothing output is predicted to soothe at least one user based, at least in part, on a set of selection criteria that are stored in computer memory;
program instructions to generate the first instance of soothing output by sending a first set of electronic signals that activate the first device, wherein, post activation, the soothing output generated by the first device (i) includes the first type of soothing output and (ii) is configured to be detectable by one or more senses of the at least one user;
program instructions to generate at least one modified selection criteria based on a given selection criteria of the set of selection criteria, wherein the given selection criteria (i) is stored in computer memory and (ii) is modified based, at least in part, on a determined level of distress of the at least one user that is determined after the first type of soothing output is generated for a time period;
program instructions to determine that a second type of soothing output is predicted to increase a level of soothing of the at least one user based, at least in part, on the at least one modified selection criteria; and
program instructions to respond to the level of distress of the at least one user at least meeting a threshold after the first type of soothing output is generated for the time period, by generating a second instance of soothing output, for the at least one user, by sending a second set of electronic signals that activate the first device, wherein the second instance of soothing output includes soothing output that is selected based on both the first type of soothing output and the second type of soothing output.

12. The computer program product of claim 11, the program instructions including:
program instructions to determine that a given soothing output is to be provided based, at least in part, on a determination that the given soothing output will soothe both the at least one user and a second user.

13. The computer program product of claim 11, the program instructions including:
program instructions to determine that the second type of soothing output is to be provided based, at least in part, on a determination that the second type of soothing output will soothe the at least one user; and
program instructions to use the first device to provide the second type of soothing output to the at least one user.

14. The computer program product of claim 13, the program instructions including:
program instructions to determine that a selection criteria of the second type of soothing output indicates that the second type of soothing output is to be provided.

15. The computer program product of claim 11, the program instructions including:
program instructions to determine a source of distress of the at least one user; and
program instructions to determine one or both of the first type of soothing output and the second type of soothing output based, at least in part, on the source of distress of the at least one user.

16. The computer program product of claim 11, the program instructions including:
program instructions to predict a future occurrence of distress for the at least one user based, at least in part, on a known source of distress for the at least one user; and
program instructions to provide one or both of the first type of soothing output and the second type of soothing output before a subsequent exposure of the at least one user to the known source of distress.

17. The computer program product of claim 11, the program instructions including:
program instructions to determine one or both of the first type of soothing output and the second type of soothing output based, at least in part, on a matching between a characteristic of the at least one user and a characteristic included in a set of records that associates user characteristics with types of soothing output, wherein the characteristic includes at least one of i) vocalizations of the at least one user, ii) movement of the at least one user, iii) a history of behavior of the at least one user, iv) a stage of development of the at least one user, v) a schedule of care activity provided for the at least one user, and vi) an environment of the at least one user.

18. The computer program product of claim 11, the program instructions including:
   program instructions to determine one or both of the first type of soothing output and the second type of soothing output based, at least in part, on a monitored soothing output that was previously provided to the at least one user by a caregiver.

19. The computer program product of claim 11, the program instructions including:
   program instructions to indicate to a caregiver of the at least one user, a third type of soothing output to be provided to the at least one user.

20. The computer program product of claim 11, the program instructions including:
   program instructions to analyze the input to determine that the at least one user is in distress, wherein the input is captured by a second device that monitors at least one of i) the at least one user, and ii) an environment of the at least one user. an environment of the at least one user.

* * * * *